US006408198B1

United States Patent
Hanna et al.

(10) Patent No.: US 6,408,198 B1
(45) Date of Patent: Jun. 18, 2002

(54) METHOD AND SYSTEM FOR IMPROVING PHOTOPLETHYSMOGRAPHIC ANALYTE MEASUREMENTS BY DE-WEIGHTING MOTION-CONTAMINATED DATA

(75) Inventors: D. Alan Hanna; Jonas A. Pologe, both of Boulder, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/632,153

(22) Filed: Aug. 3, 2000

Related U.S. Application Data (63) Continuation-in-part of application No. 09/465,883, filed on Dec. 17, 1999, now abandoned.

(51) Int. Cl.[7] .................................................. A61B 5/00
(52) U.S. Cl. ........................................ 600/323; 600/336
(58) Field of Search ................................ 600/309–310, 600/316, 322–324, 326, 328, 330, 336; 356/39–42

(56) References Cited

U.S. PATENT DOCUMENTS

| | | | |
|---|---|---|---|
| 4,846,183 A | 7/1989 | Martin | |
| 4,869,254 A | 9/1989 | Stone et al. | |
| 4,955,379 A | 9/1990 | Hall | |
| RE33,643 E | 7/1991 | Isaacson et al. | |
| 5,078,136 A | 1/1992 | Stone et al. | |
| 5,349,953 A | 9/1994 | McCarthy et al. | |
| 5,503,148 A | * 4/1996 | Pologe et al. | 600/323 |
| 5,555,882 A | 9/1996 | Richardson et al. | |
| 5,577,500 A | 11/1996 | Potratz | |
| 5,645,060 A | 7/1997 | Yorkey | |
| 5,687,722 A | * 11/1997 | Tien et al. | 600/323 |
| 5,853,364 A | * 12/1998 | Baker, Jr. et al. | 600/300 |
| 5,934,277 A | * 8/1999 | Mortz | 600/323 |

* cited by examiner

Primary Examiner—Eric F. Winakur
Assistant Examiner—Matthew Kremer
(74) Attorney, Agent, or Firm—Marsh Fischmann & Breyfogle LLP (57) ABSTRACT

A system is provided for improving photoplethysmographic analyte measurements by de-emphasizing motion-contaminated data and/or emphasizing motion-free data. The system 100 is used in a measurement instrument which includes at least illumination source 104 for transmitting at least two light signals at two center wavelengths through a patient's appendage 106 and a sensor 108 for converting the light signals transmitted through the appendage into electrical output signals. The system 100 includes a first buffer 116 configured to temporarily store at least one pulse cycle of output signals received from the sensor 108. A motion estimator 122 quantifies an amount of motion associated with the output signals stored in the first buffer 116 by performing a principal component analysis on differential absorption values derived from the output signals. Based on the amount of motion estimated, a weight application module 118 is configured to associate a weight with the output signals in the first buffer. The weighted output signals are transferred into a second buffer 120 which contains weighted output signals collected over multiple pulse cycles. An analyte computing module 126 computes blood analyte related values based on the weighted output signals stored in the second buffer 120.

36 Claims, 5 Drawing Sheets

METHOD AND SYSTEM FOR IMPROVING PHOTOPLETHYSMOGRAPHIC ANALYTE MEASUREMENTS BY DE-WEIGHTING MOTION-CONTAMINATED DATA

This application is a continuation-in-part of Ser. No. 09/465,883 filed Dec. 17, 1999 abandoned.

FIELD OF THE INVENTION

The present invention generally relates to photoplethysmographic measurement systems, and, in particular, to a method and system for improving photoplethysmographic analyte measurements by preprocessing measurement data to compensate for measurement artifact such as by de-weighting motion-contaminated data.

BACKGROUND OF THE INVENTION

In the field of photoplethysmography, light pulses from different portions of the electromagnetic spectrum are used to noninvasively determine various blood analyte related values, such as blood oxygen saturation, in test subjects. Typically, photoplethysmographic measurement systems, such as pulse oximeters, include a probe for releasably attaching to the tip of a patient's appendage (e.g., a finger, earlobe or the nasal septum). The probe directs light signals into the appendage where the probe is attached. Some portion of the light is absorbed by the tissue and a remaining portion of the light passes through patient tissue. The intensity of light passing through the tissue is monitored by a sensor typically contained in the probe. The intensity related signals produced by the sensor are used to compute blood analyte related values.

During a medical examination, measurements such as blood oxygen saturation levels computed by the pulse oximeter can be distorted by various factors including movement of the appendage where the probe is attached. For example, the movement of the patient may affect source/detector alignment, ambient light levels, blood volume fluctuation or other factors, thus resulting in potential measurement errors. Some instrument designs have attempted to address such artifact through the use of hardware such as filters to screen the detector signals. However, such approaches have generally had a limited ability to distinguish artifact components of the signal from desired information, resulting in loss of information and/or admission of substantial artifact into the data used for calculations.

SUMMARY OF THE INVENTION

There is a particular need for a photoplethysmographic measurement instrument that is capable of accurately analyzing the quality of output signals produced by an instrument sensor so that appropriate steps may be taken to improve photoplethysmographic analyte related measurements computed by the instrument. In particular, there is a need for a system with improved ability to distinguish artifact from desired information and to preprocess the data based on such distinction so as to enhance overall instrument performance.

The present invention is directed to a system and corresponding method for use in a pulse oximeter to improve the way in which data output by a pulse oximeter sensor, such as data representing a pulse waveform, is preprocessed prior to the computation of blood oxygen saturation levels. The present system quantifies artifactual components (e.g., motion artifact) contained in a set of data aggregated over a certain time interval (e.g., one or more pulse cycles or portions thereof or simply a given predetermined time interval) and preprocesses the set of data such that the effect of artifactual components is reduced. The blood oxygen saturation levels may be computed based on multiple sets of preprocessed data so as to improve the accuracy of the pulse oximetry measurements.

In accordance with one aspect of the present invention, an apparatus for evaluating the reliability of output signals produced by a pulse oximeter sensor is provided. Electrical output signals produced by the sensor may be captured at a defined interval. Each captured set of signals may be analyzed independently to estimate a degree of artifactual component reflected in the set of output signals. Unreliable sets of output signals can be addressed in a variety of ways. In one embodiment, a weight metric may be generated which accurately reflects the degree of artifactual component in the output signals. The weight metric may then be used to relatively emphasize or de-emphasize each set of output signals in proportion to the degree of artifactual component estimated such that the sets of output signals used in the blood analyte computation are dominated by output signals with a relatively small artifactual component. In another embodiment, sets of output signals that are deemed to be unreliable, i.e., the degree of artifactual component associated therewith exceeds a certain threshold, may be excluded from the blood analyte computation.

In accordance with a related aspect of the present invention, motion affected data is identified based on a numerical or mathematical analysis of the data. The electrical output signals generated by the photodetector may be separated into red and infrared data by a hardware or software based demultiplexer. The reliability of output signals may be evaluated on the basis of data points derived from separated red and infrared pulse waveforms. The motion contained in output signals produced by the pulse oximetry sensor may be quantified based on spread of the data points, e.g., from a regression model such as a best-fit linear regression line. In one embodiment, the red and infrared pulse waveforms are used to acquire differential absorption values $dA_x$ and $dA_y$, respectively. Each pulse cycle is represented by a set of data points, where each data point represents a pair of corresponding differential absorption values $dA_x$ and $dA_y$ obtained at a specific point in time within each pulse cycle. A principal component analysis ("PCS") may be performed on each set of data points to estimate an amount of motion affecting the data. First and second principal components derived from the PCA account for different amounts of variation among the set of data points. The first principal component may describe the cluster of data points disposed along a longitudinal axis and the second principal component may describe the amount of spread of the data points with respect to the longitudinal axis. An amount of motion associated with a set of data points may be approximated by multiplying the RMS (Root Mean Square) variation along the axis of the first principal component by the RMS variation along the axis of the second principal component.

According to another related aspect of the invention, a method is provided for distinguishing motion artifact from the plethysmographic signal. It has been recognized that the artifact due to motion can be distinguished from other data anomalies because motion affects tend to be relatively evenly distributed over multiple channels (a channel being the electronic or digital data received from any given emitter in a photoplethysmographic system). Accordingly, motion effects can be identified and quantified by mathematically accounting for a corresponding bias or tendency in the data. For example, if two channels of data are plotted against one another over a set of samples, motion effects tend to be reflected by a slant, e.g., an approximately 45-degree bias in the data spread since some common types of motion tend to induce similar amounts of artifact into each channel (actually into the dA's calculated from the channel data), while the plethysmographic signal will tend to spread the data at some other angle determined by blood analyte levels. It will be appreciated that such effects may be identified mathematically rather than graphically. In this regard, each data point generally includes a plethysmographic content and a motion content. The motion content of a data point may be represented by a shift of the data point at a 45-degree angle, the amount of shift indicating the degree of motion affecting the data point. Simultaneously, the data will also be spread along some other angle which is determined by blood analyte levels. The random spreading of points in two directions expands the area occupied by the points. Thus, motion artifact present in a data point may be quantified based on the area filled by the spreading of the points. Typically, a set of data points may be characterized by a parallelogram, the boundary of which encompasses a majority of data points. The amount of motion associated with such set of data points may be estimated by approximating the area of the parallelogram which outlines the data points.

According to another aspect of the invention, one or more buffers or data storage units may be utilized to temporarily store data generated by a pulse oximeter so that the data may be accessed and manipulated by processing modules to improve the accuracy of analyte related computation such as an oxygen saturation level computation. In a preferred embodiment, dual buffer system architecture is utilized. A first buffer is used to temporarily store a set of data representing at least one pulse cycle or other time period of data from a pulse oximetry sensor. A first processing module accesses the raw data stored in the first buffer to preprocess the raw data and yield preprocessed data. The preprocessed data can then be used, on a set-by-set or aggregated basis, to make the desired analyte related computations. For example, each set of preprocessed data may be transferred into a second buffer which is adapted to temporarily store multiple sets of preprocessed data most recently received from the first processing module.

The dual buffer system architecture of the present invention may be used for various purposes. For example, the data output by the sensor may be processed to eliminate, de-weight, or otherwise address data components that are not representative of the desired analyte related values, such as electronic noise, environmental noise, motion, or other artifact. In one embodiment, the first processing module may include a combination of a motion estimator and a weight application module. The motion estimator quantifies an amount of motion associated with the raw data stored in the first buffer by performing a principal component analysis on differential absorption values derived from the output signals. Based on the amount of motion estimated, the weight application module is configured to associate a weight with the raw data in the first buffer and transfer the weighted data to the second buffer. A second processing module may then assess multiple pulse cycles of improved data accumulated in the second buffer to perform its oxygen saturation level computation.

According to a further aspect of the invention, buffered or preprocessed data may be utilized to reduce the effect of artifactual component, such as motion artifact, in raw signal output by a pulse oximeter. A quantity of motion artifact identified in a set of input data, representing raw signals produced by a pulse oximeter sensor during a defined time period, may be utilized to selectively emphasize and/or de-emphasize the set of data based upon the quality of the data. In order to improve the accuracy of blood oxygen saturation computed by the pulse oximeter, the effect of data sets that are contaminated by an unacceptable amount of artifactual component may be substantially minimized or eliminated from the final computation thereof.

In one embodiment, a threshold value is used to distinguish between acceptable data (relatively free of motion) and unacceptable data (affected by motion). Data collected over each pulse cycle is considered in the blood analyte computation if the degree of motion associated therewith is below a threshold value. Otherwise, if the degree of motion exceeds the threshold, the data is discarded from further consideration in the final computation. In a preferred embodiment, weighting is used to either emphasize or de-emphasize data depending on the quantity of motion associated with the data. A quantity of motion content is estimated for each set of data stored in the first buffer. Then, a weight parameter is assigned to each set of data such that a motion-affected set of data may be relatively de-emphasized and/or a motion-free set of data is relatively emphasized. The blood analyte levels may be computed by performing a linear regression analysis on the weighted sets of data collected over multiple pulse cycles. In this regard, the slope of the best-fit line equation derived from the linear regression analysis provides an accurate blood oxygen level since the weighted sets of data are dominated by those with relative low motion content.

According to yet another aspect of the invention, processing logic may be utilized to compensate for motion-affected data. The process of estimating a quantity of motion and associating a weight parameter in proportion to the quantity of motion estimated may be embodied in the form of a software program or an executable set of instructions running on a processor. For example, a stream of pulse waveforms provided by the photodetector may be processed by a software routine configured to determine the quantity of motion artifact present in the raw data and manipulate the raw data in such a way as to produce an improved preprocessed data which more accurately reflects the actual blood oxygen saturation levels by reducing the effect of or eliminating raw data contaminated by undesirable artifactual content, i.e., due to movement of the patient.

DETAILED DESCRIPTION

Figure 1:
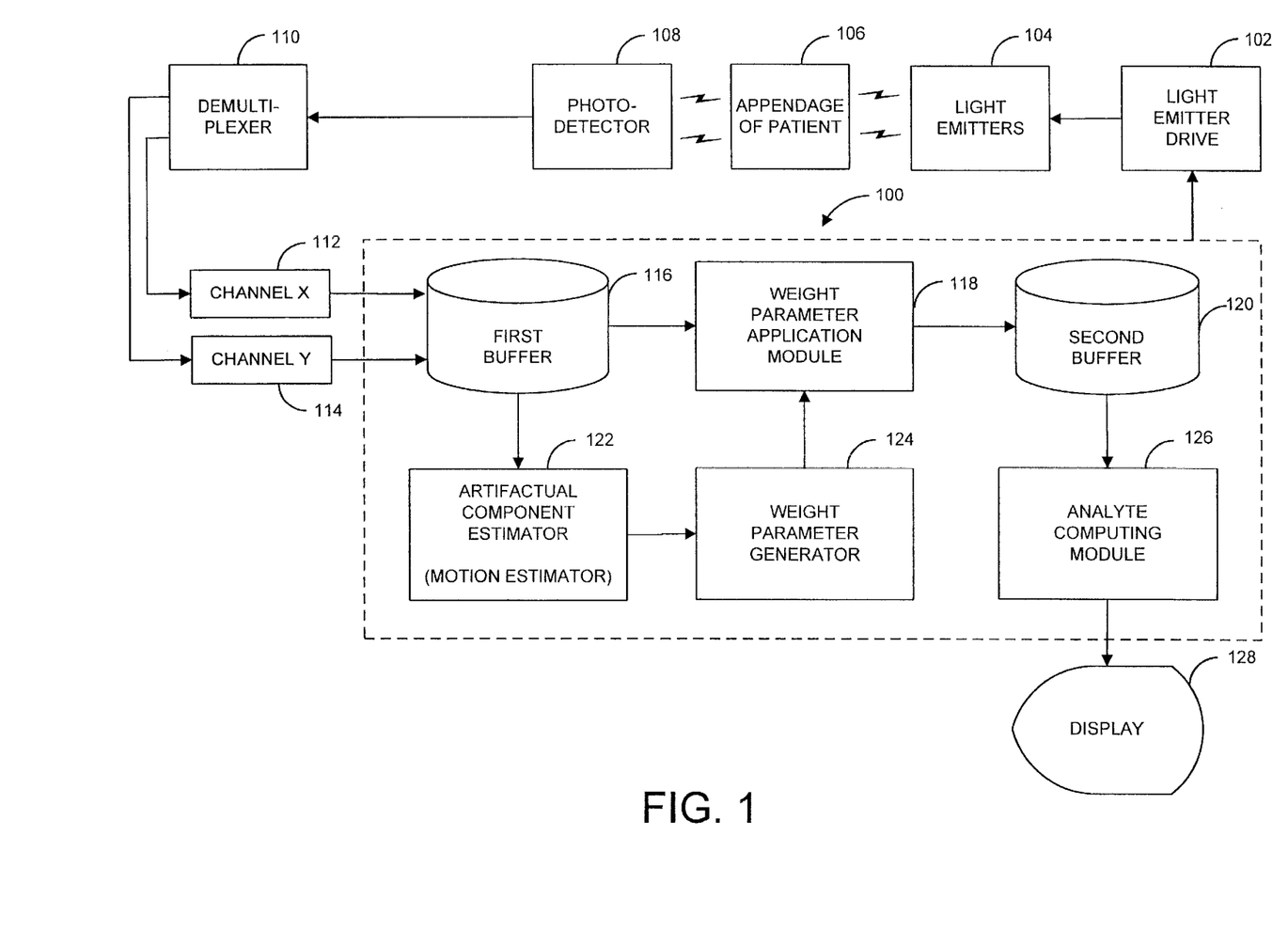
FIG. 1 is a block diagram illustrating a system for improving photoplethysmographic analyte measurements in accordance with the present invention.

Referring to FIG. 1, a system according to the present invention is generally designated at 100. The present invention is used in a photoplethysmographic measurement instrument to improve the accuracy of blood analyte values computed by the instrument by reducing the effect of artifact due to motion of a patient or due to motion of the measurement probe relative to the patient. For present purposes, the measurement instrument will be described in terms of a pulse oximeter which noninvasively measures an oxygen saturation level. Included in the illustrated pulse oximeter are one or more light emitters 104 which emit light signals at different predetermined center wavelengths. In the illustrated pulse oximeter, at least two light emitters 104 are utilized, one emitter for radiating red light and the other emitter for radiating infrared light. The light emitters may be light emitting diodes (LEDs) or laser diodes.

The pulse oximeter may include a probe which is adapted to removably attach to an appendage of a patient 106, such as a finger, earlobe, nasal septum, or other tissue, during a medical examination. In use, the probe directs the light signals generated by the light emitters onto one side of the appendage. Incorporated in the probe, on one side of the appendage is a photodetector 108 which monitors the intensity of light that is transmitted through the tissue and produces output signals corresponding to the intensity of light received.

The output signals produced by the photodetector are processed by a signal processor 110 and the resulting processed signals are transmitted to the system 100. The signal processor 110 may include, for example, amplifier circuitry, an analog to digital convertor, and other circuitry for processing the photodetector signals. As will be appreciated upon consideration of the description below, the system 100 also separately analyzes the red and infrared signals. In this regard, a hardware or software demultiplexer may be employed. In hardware implementations, the signal processor 110 may further include a demultiplexer for separating the signal into channels. In such implementations, certain other components such as A/D convertors may be duplicated for each channel. In software implementations, a composite signal including both the red and infrared components is transmitted to the system 100 and appropriate logic is used to analyze the composite signal and derive the different wavelength components therefrom. In this regard, the composite signal may be time division multiplexed, frequency division multiplexed, or other multiplexing mechanisms may be utilized.

In accordance with the present invention, one or more data storage modules (e.g. buffers) is utilized to temporarily store data generated by the photodetector 108 so that the data may be accessed and manipulated by processing modules to improve the accuracy of analyte related computations. In the illustrated embodiment, a dual buffer system architecture having a first buffer 116 and a second buffer 120 is employed. The first buffer 116 is used to temporarily store an aggregate set of data transmitted by the demultiplexer 100 during a defined time interval. The length of the defined time interval is preferably sufficient to cover at least one full plethysmographic pulse cycle, i.e., on the order of about 1.5 seconds. In particular, the first regression buffer 116 is in communication with the signal processor 110 to capture a set of data points representing the red and infrared digitized data transmitted thereby. The set of data points stored in the first regression buffer 116 may be influenced by artifact, caused by movement of the body area where the pulse oximetry probe is placed.

In the illustrated embodiment, the set of data points in the first buffer is accessed by an artifactual component estimator 122 configured to estimate an amount of artifactual component associated with the set of data points. For example, the artifactual component estimator 122 may be configured to estimate a degree of motion artifact reflected in the data points (which will be described in more detail hereinbelow). In this regard, the estimator 122 serves to analyze each captured set of data points independently in order to evaluate the reliability of output signals produced by the photodetector 108.

In one embodiment, a weight parameter generator 124 is utilized to associate a weight parameter with the set of data points in the first buffer based on the amount of artifactual component (e.g. motion) estimated. The weight parameter is used by a weight parameter application module 118 to discriminate between those data that are affected by an artifactual component and those that are relatively unaffected by an artifactual component. An unreliable set of data points can be addressed in a variety of ways. For example, the weight parameter reflecting the degree of artifactual component in the data points may be used by the module 118 to relatively emphasize or de-emphasize each set of output points. Alternatively, the module 118 may be configured to eliminate sets of data points that are deemed to be unreliable, e.g. if the degree of artifactual component associated therewith exceeds a certain threshold.

Once each set of data points has been preprocessed by the weight parameter application module 118 to compensate for the amount of artifactual component contained therein, the preprocessed set of data points is then transferred into the second buffer. The second buffer may be sized to temporarily store multiple sets of preprocessed data most recently processed by the module 118, on a FIFO basis. The preprocessed data stored in the second buffer can be used by an analyte computing module 126, on a set-by-set or aggregated basis, to make the desired analyte related computations. In one embodiment, the analyte computing module 126 is configured to processes multiple sets of data stored in a second buffer 120 accompanied by the corresponding weight parameters to compute the oxygen saturation level. Finally, the computation results made by the analyte computing module 126 are then output to a display 128.

Although the components 116, 118, 120, 122, 124 and 126 are illustrated as separate components for purposes of illustration, it will be appreciated that the components 116, 118, 120, 122, 124 and 126 may be embodied in the form of a software program or an executable set of instructions running on a processor or other logic module. For example, a stream of pulse waveforms provided by the photodetector may be processed by a software routine configured to estimate a quantity of artifactual component present in the raw data and manipulate the raw data in such a way as to produce an improved preprocessed data stream which more accurately reflects the actual blood oxygen saturation levels by reducing the effect of or eliminating raw data contaminated by undesirable artifactual content. In one embodiment, the present invention utilizes a first buffer to capture a certain time interval of the stream of pulse waveforms produced by the photodetector and utilizes a separate process to analyze and process the data stored in the first buffer and yield preprocessed data to be temporarily stored in a second buffer.

Figure 3:
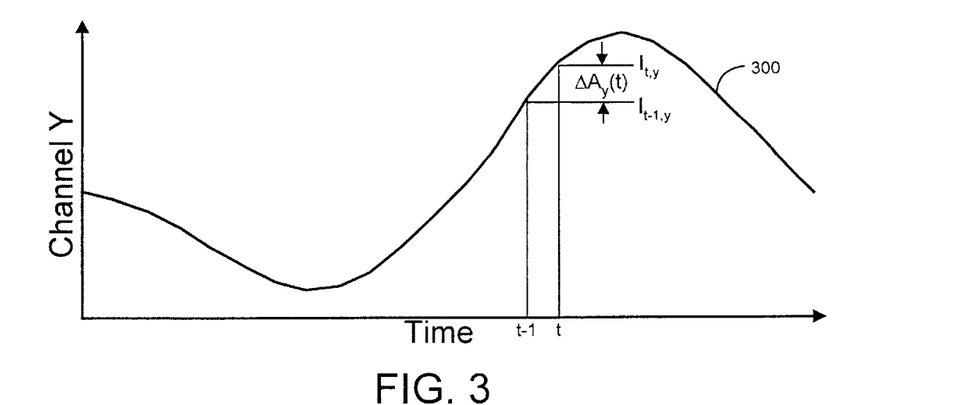
FIG. 3 is a graph illustrating an example of a pulse waveform received from the channel Y of FIG. 1.
Figure 4:
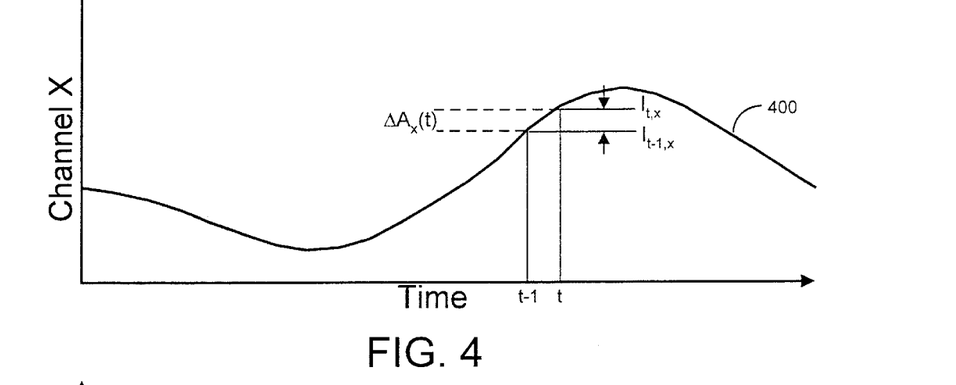
FIG. 4 is a graph illustrating an example of a pulse waveform received from the channel X of FIG. 1.

In accordance with the present invention, the process of distinguishing motion artifact from other types of artifactual components is disclosed with reference to FIGS. 3–9. Referring now to FIGS. 3 and 4, graphs of pulse waveforms 300, 400 received from the channels X and Y, respectively, as a function of time are shown. The pulse waveforms are produced by a pulse oximeter sensor as a result of light signals radiated by the red and infrared LEDs interacting with the tissue and blood carried therein. The pulse waveforms in one channel correspond to samples of red intensity and the pulse waveforms in the other channel correspond to samples of infrared intensity. The intensity signals of channels X and Y are incremented in close intervals and the differential absorption values $dA_x$ and $dA_y$ for any two adjacent data points are calculated as follows:

$$dA_x \equiv DA_x = (I_{t,x} - I_{t-1,x}) / [(I_{t,x} + I_{t-1,x})/2]$$

and similarly $$dA_y \equiv DA_y = (I_{t,y} - I_{t-1,y}) / [(I_{t,y} + I_{t-1,y})/2].$$

Although a preferred method disclosed herein uses derivatives, a ratio of the red absorption to the infrared absorption may be alternatively obtained through the use of logarithms.

Figure 5:
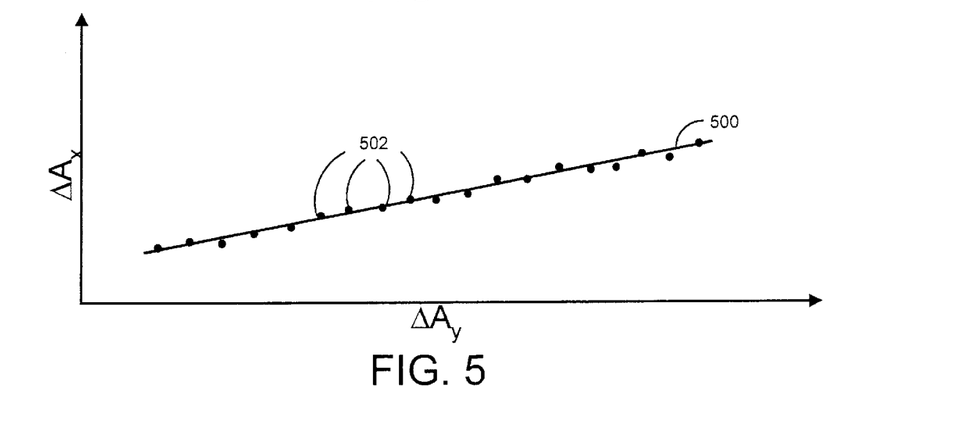
FIG. 5 is a graph illustrating an example of data points of differential absorption values $dA_x$ and $dA_y$ which are relatively unaffected by motion.

Referring to FIG. 5, a graphic representation of a linear regression analysis for computing blood analyte levels is shown. In this graph, an example of data points that are relatively unaffected by motion artifact is presented. Each data point represents a plot of a differential absorption value $dA_y$ versus a corresponding differential absorption value $dA_x$ acquired at the same or adjacent point in time. In the illustrated graph, the set of differential absorption values $dA_x$ and $dA_y$ is acquired during a short time interval, i.e., one pulse cycle. A linear regression analysis is performed on each set of the data points individually to determine a straight line 500 that best fits the set of data points, the slope of which represents the ratio of $dA_y$ and $dA_x$. This ratio of $dA_y$ and $dA_x$ may be used to determine an oxygen saturation level. These data points are tightly scattered around the best-fit line 500 indicative of good data relatively unaffected by motion or other artifacts. It should be noted that the best-fit straight line may be derived from use of any standard mathematical techniques such as a least-squares regression analysis.

Figure 6:
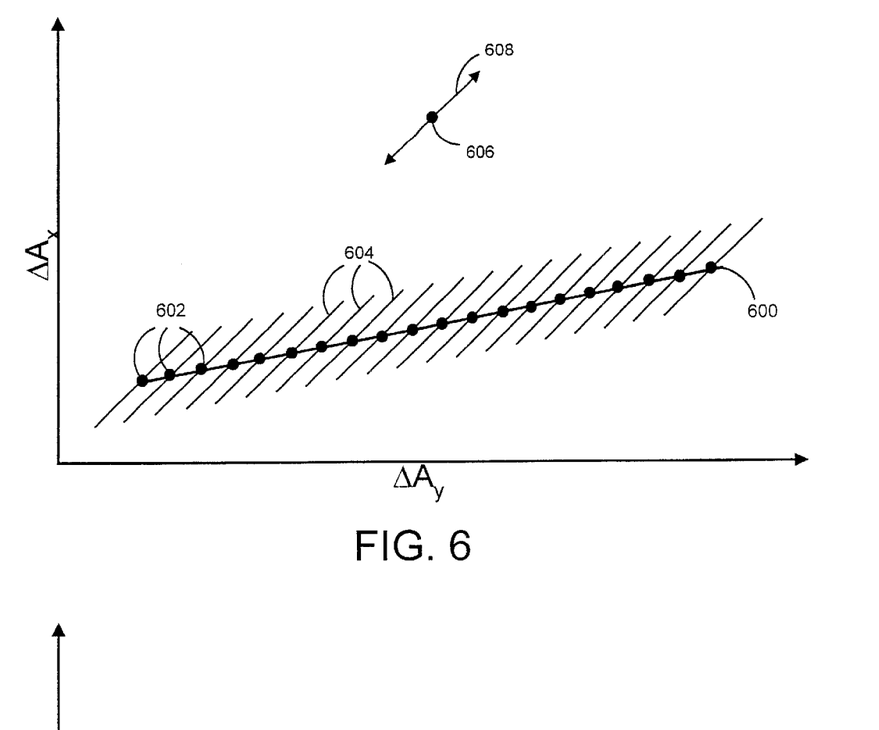
FIG. 6 is a graph illustrating a 45-degree bias contained in the data points which is caused by motion component added to the photoplethysmographic component.

An actual set of data points received from the photodetector may include an artifactual component caused by various sources, such as movement of the patient. FIG. 6 illustrates in graphical form an example of how motion affects a set of data points. It has been found that the same motion affects each differential absorption values $dA_x$ and $dA_y$ about the same, and thus a data point 606 affected by motion may be biased at, for example, a 45-degree angle, as shown by 608. Thus, data point 606 may lie anywhere along line 608 when influenced by motion artifact. The straight line 600 shows where data points should lie if no motion is present. The lines slanted, for example, in 45-degree 604 represent how the data points 602 may be displaced when data points corresponding to the ratios of the differential absorption values $dA_x$ and $dA_y$ are affected by motion.

Figure 7:
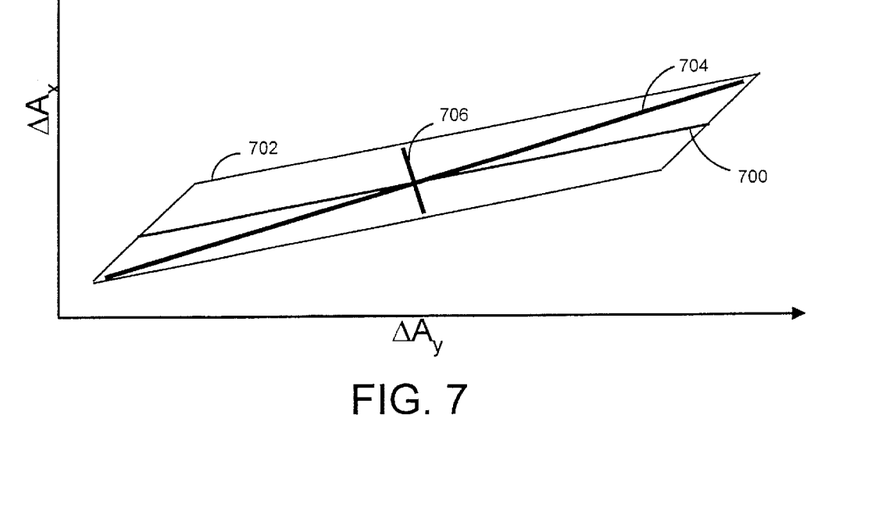
FIG. 7 is a graph illustrating first and second principal components of the data points and how they relate to a best-fit linear regression line if no motion is present in pulse waveforms.

FIG. 7 graphically illustrates a principal component analysis ("PCA") performed on a set of data points to estimate the amount of motion. The set of data points distributed within a two-dimensional space is described using first 704 and second 706 principal component vectors derived from the PCA. Each of the principal component vectors accounts for a different amount of variation among data points. The first principal component vector 704 describes the cluster of data points disposed along a longitudinal axis. The second principal component vector 706 extends perpendicular to the first principal component, the equation of which is used to describe the spread of data points with respect to the longitudinal axis.

With vectors describing variations among the set of data points in different directions, any number of algorithms may be used to estimate an amount of motion associated therewith. In one embodiment, the area of the parallelogram 702 defining the region in which the data points are distributed is used to quantify the motion associated with the set of data points. For example, the area of the parallelogram 702 may be approximated by multiplying the length of the first principal component vector by the length of the second principal component vector.

Figure 8:
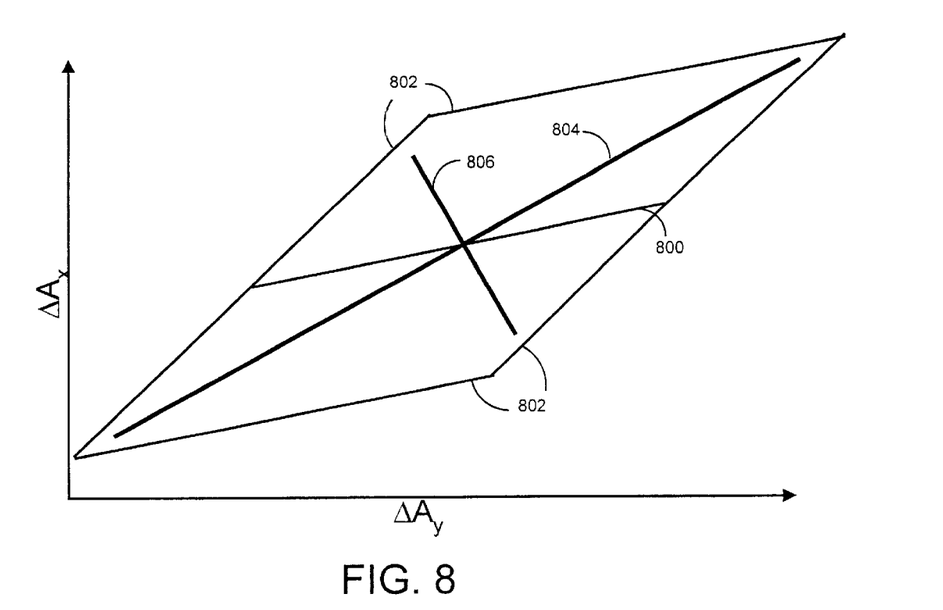
FIG. 8 is a graph illustrating an example of data points which are affected by relatively large amounts of motion.

Referring to FIG. 8, an example of data points affected by relatively large amounts of motion is shown. The straight line that would best fit the set of data points if the motion contents thereof are eliminated is represented by a line 800. However, if a linear regression analysis is performed on the motion-affected data points, a line 804 is identified as the best-fit line. The difference between the slope of the line 800 and the line 804 becomes greater as the magnitude of the motion content of the data points becomes greater, thereby destroying the correct relationship between the red and infrared intensity signals. Thus, the accuracy of the measurement readings produced by a pulse oximeter can be severely compromised by motion of such magnitude. The area of the parallelogram 802 may be used to estimate a degree of motion affecting the data. Incremental increase in the area of the parallelogram indicates an incremental reduction in the quality of data due to motion artifact contained therein.

A number of different methods for estimating the motion content of data are possible. As noted above, one way of obtaining a motion content of data is by performing a principal component analysis, in which the motion metric may be computed by multiplying the RMS variation along the axis of the first principle component by the RMS variation along the axis of the second principle component. It should be understood that the essence of the method is that motion is estimated according to the increase in the scatter of the points in several dimensions. Any method that gauges the increase in dA scatter to judge motion is within the spirit of the invention.

In order to compensate for data distorted by motion, the data may be excluded or de-weighted based on the degree of motion estimated. In a preferred embodiment, the data is processed using a weighting function which tends to emphasize data which is relatively unaffected by motion and de-weight data which is more affected. A weighting factor is computed from the motion metric. The weighting factor is used to de-emphasize data when high motion levels are detected. In one embodiment, the data points are multiplied by the inverse of the square of the motion metric. In another embodiment, the motion metric is compared against a threshold value. The threshold value is used to distinguish between motion-free and motion-affected pulse waveforms. Pulse waveforms are valid if the corresponding motion content is below a certain threshold value. In which case, the corresponding ratio of $dA_y$ to $dA_x$ is used in the blood analyte computation. The pulse waveforms that are beyond an acceptable limit are disregarded from further consideration in the blood analyte computation.

Figure 9:
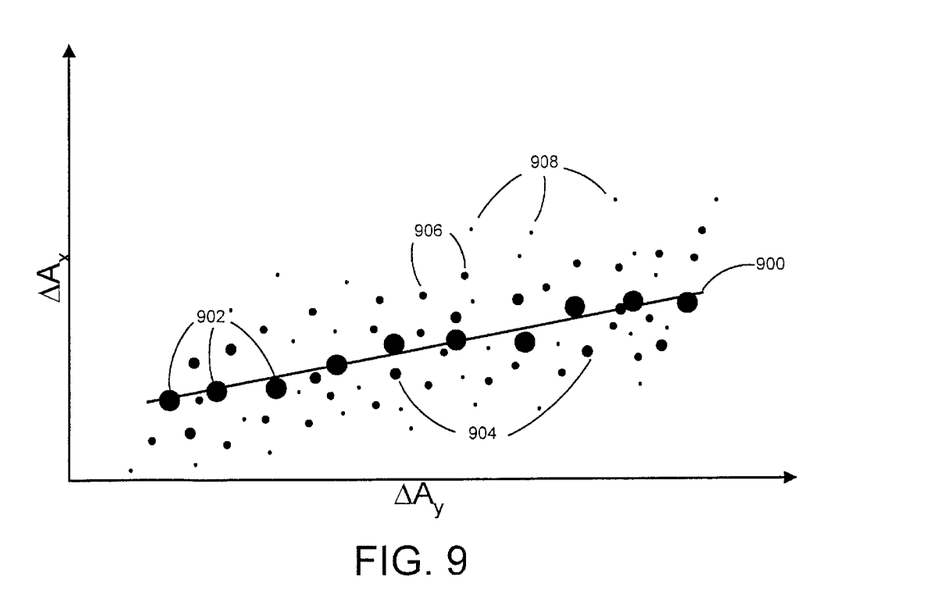
FIG. 9 is a graph illustrating weighted data points temporarily stored in the second regression buffer and a linear regression line that best fits the weighted data points.

FIG. 9 graphically illustrates the weighted data points stored in the second regression buffer. A linear regression analysis is performed on the weighted data points to obtain a best-fit line 900. The data points in the second regression buffer are dominated by data with low motion content. The second buffer contains data in which motion-free sets of data points 902, 904 are highly weighted (or emphasized) and motion-contaminated sets of data points 906, 908 are de-weighted or excluded. Motion-free points are shown as large dots, motion-contaminated data by smaller dots. The straight line fit relies most on the largest dots. Blood analyte levels can then be computed based on a linear equation yielding a best-fit line 900. The second regression buffer holds information taken from the first regression buffer over multiple plethysmographic cycles, on the order of 3 to 30 seconds. Because the data transferred from the first regression buffer are accompanied by their respective motion weighting factors (or, alternatively, consists only of data with acceptable low levels of motion), analyte computation performed using values in the second regression buffer are dominated by data with low motion content. The time interval covered by the second regression buffer is preferably long enough to encompass some motion-free data along with typical motion-contaminated data, but not so long as to provide blood analyte readings for an excessive time after such readings have ceased to be valid. In fact, the length of the second regression buffer may be dynamically variable depending on and proportional to, the quantity of motion present in the data.

Figure 2:
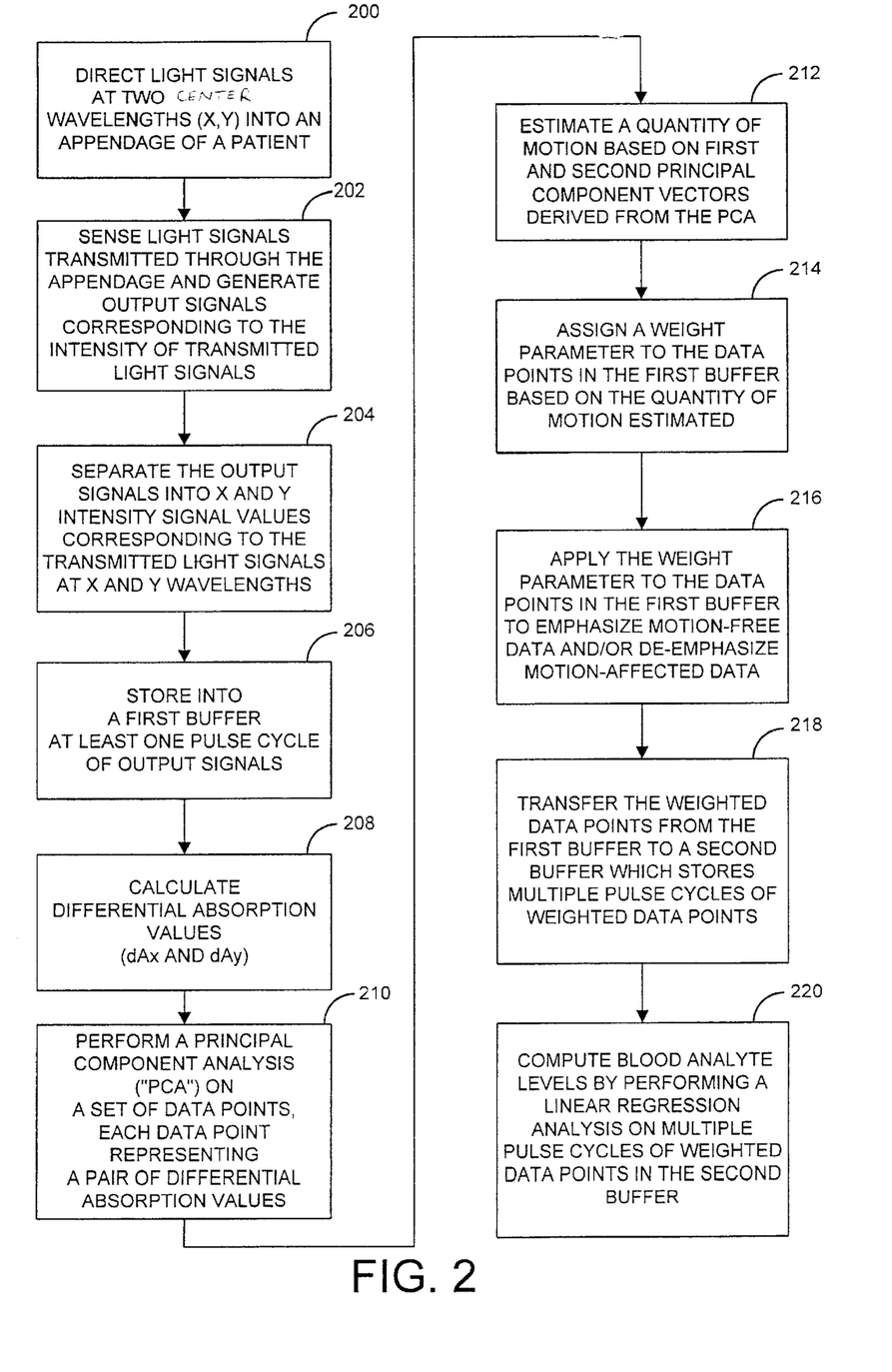
FIG. 2 is a flow diagram illustrating the general steps involved in obtaining improved photoplethysmographic analyte measurements in accordance with the present invention.

The operation of the system of the present invention may be better understood by reference to FIG. 2. Disclosed therein is a flowchart diagram which illustrates operation of the system for improving photoplethysmographic analyte measurements. To perform measurement of the blood analyte levels, a probe attached to a patient's appendage is used to direct the light signals generated by the light emitters at X and Y center wavelengths to an appendage of a patient under examination in step 200. In step 202, the photodetector receives the light signals transmitted through the patient's appendage and converts the received light signals into analog output signals. The analog output signals produced by the photodetector include a plethysmographic component having characteristics that are a function of the level of the blood analyte of interest. In addition to the plethysmographic component, the output signals may also include a motion component attributable to movement of the appendage where the probe is attached. In step 404, the output signals are separated into red and infrared pulse waveforms and digitized by an analog-to-digital converter prior to preprocessing of the raw data from the photodetector.

At this point and in step 206, the red and infrared pulse waveforms aggregated over a time period at least equal to or exceeding one pulse cycle (although it is possible to use even less) are temporarily stored in the first data buffer. Then in step 208, the red and infrared pulse waveforms are used to calculate differential absorption values $dA_x$ and $dA_y$. In step 210, a principal component analysis is performed on the differential absorption values stored in the first buffer. Based on the principal component analysis, a degree of motion content contained in the current set of data is estimated based on first and second principal component vectors derived from the PCA (step 212). Based on the degree of motion estimated, a weight parameter is assigned (step 214). Then in step 216, the weight parameter application module multiplies each set of raw data in the first buffer by the corresponding weight parameter to emphasize motion-free raw data and/or de-emphasize motion-affected raw data to reduce the influence of motion-affected raw data. Next in step 218, the set of data is transferred from the first buffer to the second regression buffer. Finally in step 220, the blood oxygen saturation levels are determined by performing a linear regression analysis on multiple pulse cycles of the weighted sets of data points in the second buffer.

It should be noted that in addition to the application in reducing motion artifact contained in output signals produced by a pulse oximeter sensor, the dual buffer architecture of the present system has other applications where it is desirable to process a set of raw data collected in a first data storage area to provide a preprocessed data set which may be used with other preprocessed data sets accumulated over a certain time period in a second data storage area to ultimately perform mathematical computations to provide an accurate analyte measurement. It is possible that the subsystem modules 118, 122, 124 (FIG. 1) may be replaced with any other suitable combinations of processing modules capable of accessing a set of data stored in the first buffer 116 and processing it so as to provide an improved set of data which may be ultimately used by the analyte computing module 126 to provide a more accurate blood oxygen saturation level.

It should also be obvious to one familiar with the processing of digital data, that the "second regression buffer" simply refers to the photoplethysmographic data after it is processed by calculating the artifactual content regardless of the exact form or duration of the storage of these data.

While the foregoing preferred embodiments of the invention have been described and shown, it is understood that variations and modifications, such as those suggested and others within the spirit and scope of the invention, may occur to those skilled in the art to which the invention pertains. The scope of the present invention accordingly is to be defined as set forth in the appended claims.

What is claimed is:

1. An apparatus for use in a measurement instrument which includes at least one illumination source for generating a plurality of light signals at least at two different center wavelengths corresponding to at least two different channels and transmitting said light signals relative to a tissue of a test subject and a sensor configured to receive said light signals transmitted relative to the tissue and to convert the light signals received into output signals, said apparatus comprising:

a first data storage for storing input data sets representing multiple determined time periods of said output signals, each of said input data sets including first channel data including multiple values based on a first one of said light signals corresponding to a first one of said channels and second channel data including multiple values based on a second one of said light signals corresponding to a second one of said channels;

a first processor configured to receive said input data from said first data storage and perform a multichannel noise analysis involving said first channel data and said second channel data for each of said data sets, and to thereby process said input data sets to output processed data, where said processed data includes multiple output data sets, corresponding to a plurality of said determined time periods, which are selectively modified on a set-by-set basis based on said multichannel noise analysis;

a second data storage for storing said processed data output by said first processor corresponding to said plurality of said determined time periods; and a second processor for computing a blood analyte related value of the test subject based on said processed data stored in said second data storage.

2. The apparatus of claim 1, wherein each said input data set stored in said first data storage represents at least a significant portion of one pulse cycle of said output signals produced by the sensor.

3. The apparatus of claim 1, wherein the measurement instrument is a pulse oximeter for noninvasively measuring a blood oxygen saturation in the tissue of the test subject.

4. The apparatus of claim 1, wherein said first processor is configured to estimate a degree of an artifactual component reflected in said input data and process said input data sets such that said blood analyte computation is dominated by one or more of said input data sets with a relatively small artifactual component.

5. The apparatus of claim 4, wherein said artifactual component estimated by said first processor is due to motion of the test subject where the sensor is attached.

6. The apparatus of claim 1, wherein said first processor is configured to estimate a degree of motion associated with said input data and generate a corresponding motion factor based on said degree of motion estimated.

7. The apparatus of claim 6, wherein said processed data output by said first processor represents said input data after said motion factor is used to relatively emphasize or de-emphasize said input data in proportion to the degree of motion estimated.

8. The apparatus of claim 6, wherein said processed data output by said first processor represents said input data after said motion factor is used to eliminate said input data from the blood analyte computation if the degree of motion estimated associated therewith exceeds a determined threshold.

9. The apparatus of claim 6, wherein the degree of motion is estimated based on an assumption that motion affects each of the first and second pulse waveforms substantially the same.

10. The apparatus of claim 1, wherein the output signals produced by the sensor are separated into first and second pulse waveforms respectively representative of the light signal emitted at first and second wavelengths after being absorbed by said tissue.

11. The apparatus of claim 10, further comprising means for computing a set of data points from first and second pulse waveforms, each data point representative of a pair of differential absorption values of said first and second pulse waveforms.

12. The apparatus of claim 11, wherein said first processor is configured to determine a degree of variation among said set of data points with respect to a best-fit linear regression line.

13. The apparatus of claim 11, wherein said first processor is configured to determine a first degree of variation among said set of data points in one direction and a second degree of variation among said set of data points in another direction perpendicular to said one direction, wherein said degree of motion associated with said at least one pulse cycle of output signals is proportional to a product of said first and second degree of variations.

14. The apparatus of claim 11, wherein said second processor computes the blood analyte related value by determining a slope of a line which best fits a plurality of sets of data points after each individual set of data points is emphasized or de-emphasized based on the degree of motion associated therewith and computing the blood analyte related value based on said slope of the best-fit line.

15. An apparatus for determining the reliability of output signals produced by a pulse oximeter sensor, comprising:
    means for receiving output data from said pulse oximeter sensor corresponding to first and second determined time periods, said output data including a first data set including a plurality of first data values for said first time period and a second data set including a plurality of second data values for said second time period;
    means for analyzing said first and second data sets to estimate corresponding degree of artifactual component reflected in said first and second data sets and apply respective first and second weights to said first and second data sets; and
    a processor for using said first and second data sets and said first and second weights to make a determination of a blood analyte relate value, where said first and second data values are attributed different weights in said determination.

16. The apparatus of claim 15, wherein said means for analyzing further comprises:
    means for separating the output signals produced by the pulse oximeter into first and second pulse waveforms respectively representative of light signals emitted at first and second center wavelengths after being absorbed by a tissue of a test subject;
    means for obtaining a set of data points from first and second pulse waveforms, wherein each respective one of said data points represents a pair of differential absorption values derived from said first and second pulse waveforms;
    means for determining a degree of variation among said set of data points with respect to a best-fit linear regression line.

17. The apparatus of claim 16, wherein said artifactual component is caused by motion of the test subject where the sensor is attached and said degree of artifactual component is estimated based on an assumption that motion affects each of the first and second pulse waveforms substantially the same.

18. The apparatus of claim 17, wherein said means for analyzing further comprises:
    means for determining a first degree of variation among said set of data points in one direction; and
    means for determining a second degree of variation among said set of data points in another direction perpendicular to said one direction, wherein said degree of artifactual component associated with said output signals is proportional to a product of said first and second degree of variations.

19. A pulse oximeter for noninvasively measuring a blood analyte related value in a tissue of a test subject, comprising:
    at least one illumination source for generating at least two light signals at predetermined center wavelengths and for transmitting said light signals through the tissue;
    a sensor configured to receive said light signals transmitted through the tissue and to convert the light signals received into output signals; and
    a processor configured to receive a plurality of input data sets, each of said input data sets representing a determined time period of said output signals produced by said sensor and to preprocess each respective input data set by applying different weights to each said set to thereby establish a preprocessed data output reflecting said different weights;
    wherein said blood analyte related value is computed based on said preprocessed data reflecting said different weights.

20. The pulse oximeter of claim 19, wherein said processor is configured to evaluate the quality of each of said input data sets individually based on a mathematical analysis thereof.

21. The pulse oximeter of claim 19, wherein the processor is configured to separate said output signals into first and second pulse waveforms and to estimate a quantity of motion associated with each of said input data sets based on an assumption that motion affects each of the first and second pulse waveforms substantially the same.

22. The pulse oximeter of claim 21, wherein a weight parameter is assigned to each of said input data sets based on said quantity of motion estimated, and said weight parameter is used to accomplish at least one of the following: emphasize output signals that are not affected by motion and de-emphasize output signals that are affected by motion relative to said quantity of motion estimated.

23. A method for improving the accuracy of a blood analyte related value measured by a pulse oximeter having an illumination source for transmitting light signals of at least at two different predetermined center wavelengths relative to tissue of a test subject and a sensor configured to receive the light signals transmitted relative to the tissue and to convert the light signals received into output signals, said method comprising the steps of:

based on said output signals, storing a first data set corresponding to a first time period and a second data set corresponding to a second time period in a first memory;

processing said first and second data sets stored in said first memory to generate a processed data set, for storage in second memory, based on but different than said first and second data sets; and;

computing said blood analyte related value for the tissue of the test subject based on said processed data set, where said first and second data sets are weighted differently in said step of computing.

24. The method of claim 23, wherein said processing step further comprises the step of identifying motion affected output signals based on a mathematical analysis of said determined time period of said output signals.

25. The method of claim 23, wherein said processing step further comprises the step of estimating a quantity of motion associated with said determined time period of said output signals based on said mathematical analysis thereof.

26. The method of claim 25, wherein said processing step further comprises at least one of the following steps:

emphasizing said output signals according to said corresponding quantity of motion estimated; and de-emphasizing said output signals according to said corresponding quantity of motion estimated.

27. The method of claim 25, wherein said processing step further comprises the step of eliminating said determined time period of said output signals from the blood analyte related value computation if the quantity of motion estimated associated therewith exceeds a determined threshold.

28. The method of claim 23, wherein said processing step is accomplished with a processor in connection with said first memory.

29. The method of claim 28, further comprising the step of accumulating in a second memory a plurality of said processed data output by said processor, wherein said blood analyte related value is computed based on said plurality of said processed data stored in said second memory.

30. The method of claim 23, further comprising the step of separating said output signals into first and second pulse waveforms respectively representative of light signals emitted at first and second wavelengths after being absorbed by said tissue.

31. The method of claim 30, wherein the processing step further comprises the step of evaluating the reliability of said output signals based on a mathematical analysis of said first and second pulse waveforms.

32. The method of claim 31, wherein the reliability of said output signals is evaluated on the basis of a quantity of motion associated with said output signals.

33. The method of claim 32, wherein the quantity of motion associated with said output signals is estimated based on an assumption that motion affect each of the first and second pulse waveforms substantially the same.

34. The method of claim 32, wherein said evaluating step further comprises the steps of:

deriving a set of data points from said first and second pulse waveforms, each data point representative of a pair of differential absorption values of said first and second pulse waveforms; and estimating said quantity of motion associated with said set of data points based on a degree of variation among said set of data points with respect to a best-fit linear regression line.

35. The method of claim 34, wherein the evaluating step further comprises the steps of:

using said first and second waveforms to acquire pairs of differential absorption values $dA_x$ and $dA_y$;

approximating a degree of motion artifact associated with the output signals based on the concentration of the pairs of differential absorption values $dA_x$ and $dA_y$ along a best-fit linear line.

36. The method of claim 32, wherein the processing step further comprises at least one of the following steps:

emphasizing the output signals that are determined to be reliable in the evaluating step;

de-emphasizing the output signals that are determined to be unreliable in the evaluating step; and eliminating the output signals that are determined to be unreliable in the evaluating step.

* * * * *